US012648714B2

(12) United States Patent
Rajguru et al.

(10) Patent No.: US 12,648,714 B2
(45) Date of Patent: Jun. 9, 2026

(54) INTRAVASCULAR IMAGING PROCEDURE-SPECIFIC WORKFLOW GUIDANCE AND ASSOCIATED DEVICES, SYSTEMS, AND METHODS

(71) Applicant: PHILIPS IMAGE GUIDED THERAPY CORPORATION, San Diego, CA (US)

(72) Inventors: Nikhil Sreedhar Rajguru, Rancho Cordova, CA (US); Asher Cohen, San Francisco, CA (US); Sara Rose Chen, San Diego, CA (US); Pei-Yin Chao, Eindhoven (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 18/752,259

(22) Filed: Jun. 24, 2024

(65) Prior Publication Data

US 2024/0341629 A1 Oct. 17, 2024

Related U.S. Application Data

(63) Continuation of application No. 18/206,175, filed on Jun. 6, 2023, now Pat. No. 12,016,675, which is a continuation of application No. 16/520,472, filed on Jul. 24, 2019, now Pat. No. 11,666,245.

(60) Provisional application No. 62/712,009, filed on Jul. 30, 2018.

(51) Int. Cl.
A61B 5/00 (2006.01)
A61B 5/02 (2006.01)
A61B 5/107 (2006.01)

(52) U.S. Cl.
CPC .......... *A61B 5/1076* (2013.01); *A61B 5/0084* (2013.01); *A61B 5/02007* (2013.01); *A61B 5/1079* (2013.01); *A61B 5/6852* (2013.01)

(58) Field of Classification Search
CPC .................................................... A61B 5/1076
See application file for complete search history.

(56) References Cited

U.S. PATENT DOCUMENTS

| | | | |
|---|---|---|---|
| 7,846,101 B2 | 12/2010 | Eberle | |
| 9,138,147 B2 | 9/2015 | Schmitt | |
| 2008/0101667 A1* | 5/2008 | Begelman | ................. G06T 7/11 |
| | | | 600/407 |
| 2014/0100442 A1 | 4/2014 | Begin | |
| 2015/0073279 A1 | 3/2015 | Cai | |

(Continued)

FOREIGN PATENT DOCUMENTS

| | | |
|---|---|---|
| WO | 2014137353 A1 | 9/2014 |
| WO | 2017130927 A1 | 8/2017 |

*Primary Examiner* — Joseph M Santos Rodriguez

(57) ABSTRACT

Systems, devices, and methods for providing procedure-specific workflow guidance are provided. The workflow guidance may include providing selectable options on a display device to a user including a selectable option to select a target vessel and a prompt to move an intravascular imaging device within the selected target vessel. Imaging data is received from the intravascular imaging device within the selected target vessel. The workflow guidance may be used to identify an area of interest within the selected target vessel and automatically display vessel measurements corresponding with the area of interest on the display device.

13 Claims, 12 Drawing Sheets

(56) References Cited

U.S. PATENT DOCUMENTS

| | | | |
|---|---|---|---|
| 2015/0133776 A1 | 5/2015 | Hoffman | |
| 2015/0331995 A1 | 11/2015 | Zhao | |
| 2016/0007967 A1 | 1/2016 | Johnson | |
| 2016/0022208 A1 | 1/2016 | Gopinath | |
| 2016/0157787 A1* | 6/2016 | Merritt | A61B 5/02007 |
| | | | 600/481 |
| 2016/0157807 A1 | 6/2016 | Anderson | |
| 2018/0085170 A1 | 3/2018 | Gopinath | |
| 2018/0344174 A9 | 12/2018 | Schmitt | |
| 2019/0282182 A1 | 9/2019 | Scott | |
| 2019/0282199 A1 | 9/2019 | Merritt | |
| 2019/0282211 A1 | 9/2019 | Merritt | |
| 2020/0029932 A1 | 1/2020 | Cohen | |

* cited by examiner

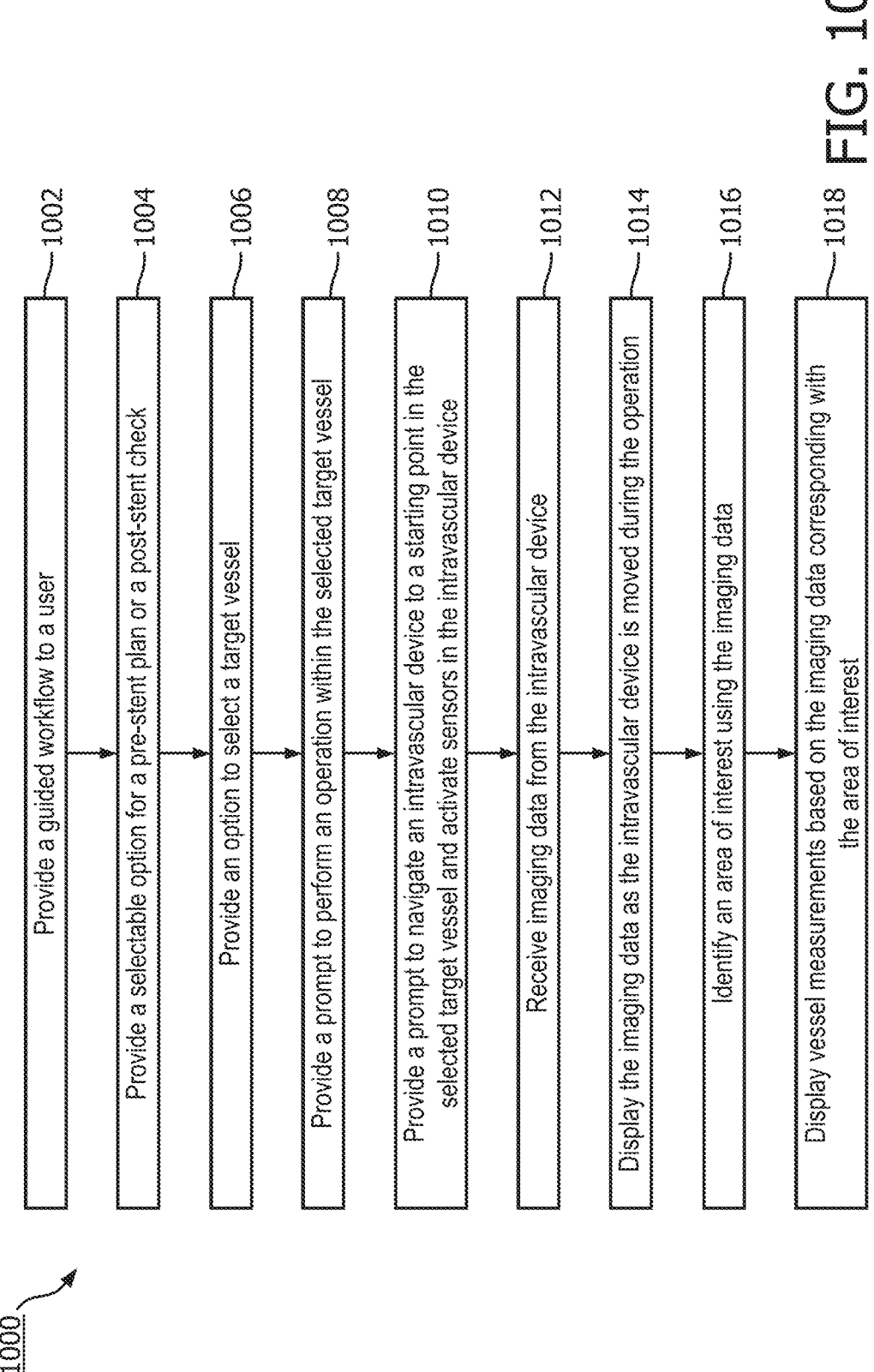

1002 — Provide a guided workflow to a user

1004 — Provide a selectable option for a pre-stent plan or a post-stent check

1006 — Provide an option to select a target vessel

1008 — Provide a prompt to perform an operation within the selected target vessel 1010 — Provide a prompt to navigate an intravascular device to a starting point in the selected target vessel and activate sensors in the intravascular device 1012 — Receive imaging data from the intravascular device 1014 — Display the imaging data as the intravascular device is moved during the operation 1016 — Identify an area of interest using the imaging data 1018 — Display vessel measurements based on the imaging data corresponding with the area of interest

INTRAVASCULAR IMAGING PROCEDURE-SPECIFIC WORKFLOW GUIDANCE AND ASSOCIATED DEVICES, SYSTEMS, AND METHODS

CROSS-REFERENCE TO PRIOR APPLICATIONS

This application is a continuation of U.S. application Ser. No. 18/206,175, filed 6 Jun. 2023, now U.S. Pat. No. 12,016,675, which is a continuation of U.S. application Ser. No. 16/520,472, filed 24 Jul. 2019, now U.S. Pat. No. 11,666,245, which claims the benefit of U.S. Provisional Application No. 62/712,009, filed on 30 Jul. 2018. These applications are hereby incorporated by reference herein.

TECHNICAL FIELD

The present disclosure relates generally to obtaining intravascular data associated with a body vessel of a patient, and, in particular, to providing a workflow to a user to perform an intravascular imaging procedure with an intravascular imaging device. The workflow may be displayed to a user as prompts and instructions as well as visualizations of imaging data from the intravascular imaging device.

BACKGROUND

Various types of intravascular imaging systems are used in diagnosing and treating diseases. For example, intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy and receive ultrasound echoes reflected from the vessel. The ultrasound echoes are processed to create an image of the vessel of interest.

The advent of faster computational analysis has increased the effectiveness of intravascular imaging systems. However, existing intravascular imaging systems typically require operators to have a high degree of skill and experience to safely operate intravascular devices. For example, depending on the type of operation, the performance of an intravascular procedure may include many steps including maneuvering devices, measurements, and analysis of results. An operator must know and complete all of these steps to successfully perform the procedure. The large number and complexity of steps may make these procedures difficult to perform and may cause errors in the procedures.

SUMMARY

Systems, devices, and methods for providing instructions for an operator of an intravascular imaging system are provided. The intravascular imaging system may include a controller configured to provide a selectable options on a display device to select a target vessel, identify an area of interest within the selected target vessel based on the received imaging data, and automatically display, in response to identifying the area of interest, vessel measurements corresponding with the area of interest on the display device. Aspects of the present disclosure advantageously provide complete end-to-end workflow solutions that overcome the limitations of existing intravascular imaging systems.

Embodiments of the present disclosure provide an intravascular imaging system, which may include: a controller in communication with an intravascular imaging device, the controller configured to: provide, on a display device in communication with the controller, a selectable option to select a target vessel; provide a prompt to move the intravascular imaging device within the selected target vessel; receive imaging data from an imaging sensor during movement of the intravascular imaging device within the selected target vessel; identify an area of interest within the selected target vessel based on the received imaging data; and automatically display, in response to identifying the area of interest, vessel measurements corresponding with the area of interest on the display device.

In embodiments, the intravascular imaging system further includes the intravascular imaging device, including: a flexible elongate member configured to be inserted into the target vessel of a patient; the imaging sensor disposed on a distal portion of the flexible elongate member; and the display device. The controller may be further configured to provide a selectable option on the display device to perform a pre-stent procedure or a post-stent check. The controller may be further configured to automatically measure a diameter of the vessel within the area of interest, determine a first location within the area of interest with a minimum diameter, and display the first location and the minimum diameter on the display device.

In some embodiments, the display of the vessel measurements is configured to allow a user to edit a depiction of a border of the vessel. The display of the vessel measurements may include a first view and a second view of the area of interest different from the first view. A user's edit to the depiction of the border of the vessel may be displayed in the first view and the second view of the area of interest. The display of the vessel measurements may include a depiction of a target area for a stent if a user selects the pre-stent procedure option. The display of the vessel measurements may include a depiction of a stent if a user selects the post-stent check option. The display of the vessel measurements may further include a depiction of a stent malapposition.

A method of intravascular imaging is also provided, which may include: providing, with a controller in communication with an intravascular imaging device, a selectable option on a display device to select a target vessel within a patient; providing, with the controller, a prompt to move the intravascular imaging device in the selected target vessel on the display device; receiving, with the controller, imaging data from an imaging sensor while the intravascular imaging device is moved within the selected target vessel; identifying, with the controller, an area of interest within the selected target vessel based on the received imaging data; and displaying automatically, with the display device, vessel measurements corresponding with the area of interest.

The method may also include providing, with a controller, a selectable option on a display device to perform a pre-stent procedure or a post-stent check. The method may include measuring, with the controller, a diameter of the vessel within the area of interest, identifying a first location with a minimum diameter within the area of interest; and displaying the first location and minimum diameter on the display device. The method may include providing, with the controller, an option to edit a depiction of a border of the vessel on the display device.

In some embodiments, the display of the vessel measurements includes a first view and a second view of the area of interest different from the first view. The method may include displaying an edit to the depiction of the border of the vessel in the first view and the second view of the area of interest. The method may include displaying the edit to the depiction of the border of the vessel in a third view different from the first view and the second view. The display of the vessel measurements may include a depiction of a target area for a stent if a user selects the pre-stent procedure option. The display of the vessel measurements may include a depiction of a stent if a user selects the post-stent check option. The display of the vessel measurements further may include a depiction of a stent malapposition.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 7B is an exemplary illustration of another display showing various views of imaging data according to aspects of the present disclosure.

FIG. 10 is a flow diagram of a method of providing a guided workflow according to aspects of the present disclosure.

DETAILED DESCRIPTION

Figure 1:
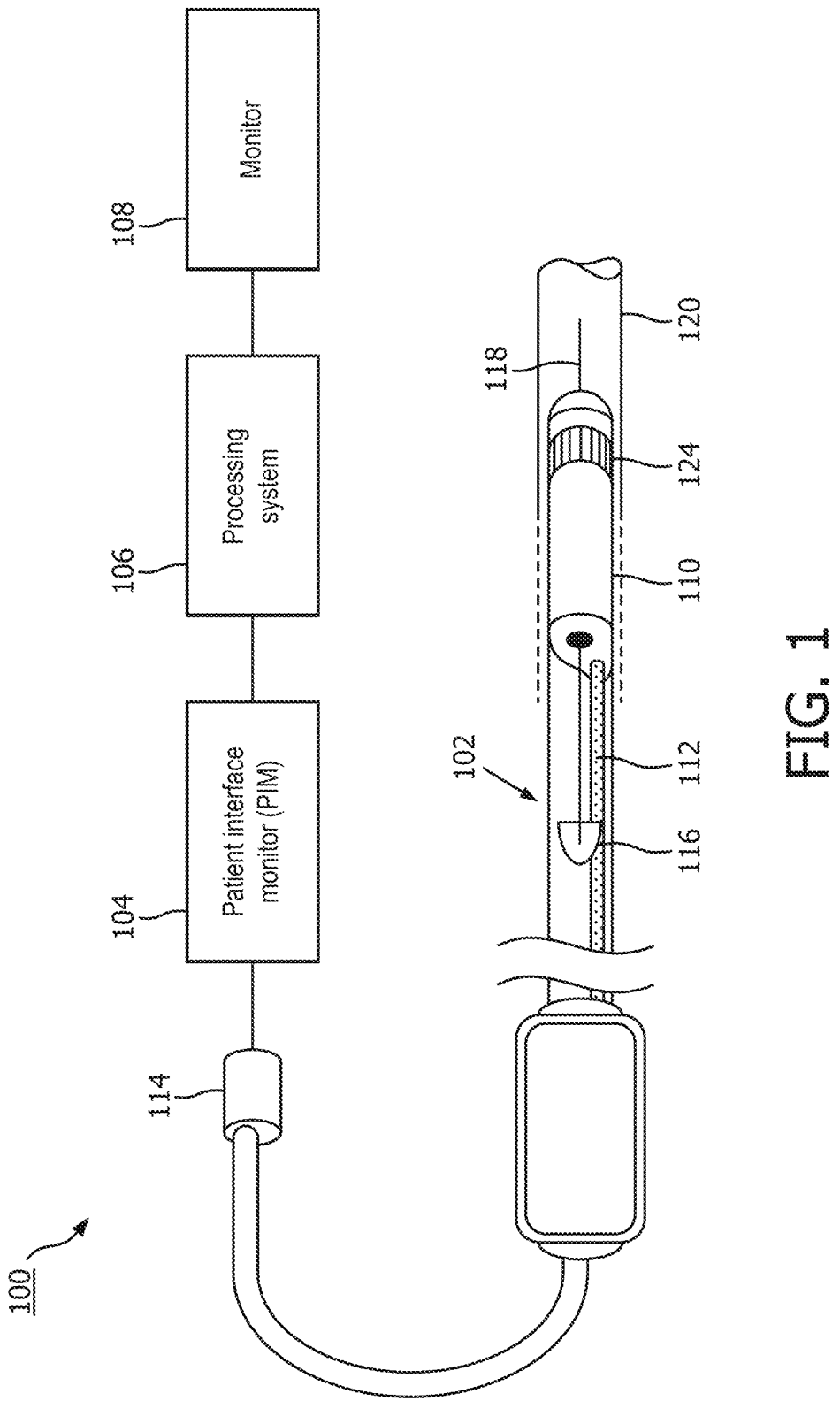
FIG. 1 is a diagrammatic schematic view of an intravascular imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intravascular imaging system 100, according to aspects of the present disclosure. The intravascular imaging system 100 may include an intravascular device 102, a patient interface module (PIM) 104, a console or processing system 106, and a display device or monitor 108. The intravascular device 102 may be sized and shaped, and/or otherwise structurally arranged or configured to be positioned within a body lumen 120 of a patient. For example, the intravascular device 102 can be a catheter, guide wire, guide catheter, pressure wire, and/or flow wire in various embodiments. In some circumstances, the system 100 may include additional elements and/or may be implemented without one or more of the elements illustrated in FIG. 1.

The devices, systems, and methods described herein can include one or more features described in U.S. Provisional App. No. 62/643,105, filed on an even date herewith, U.S. Provisional App. No. 62/642,847, filed on an even date herewith, U.S. Provisional App. No. 62/711,927, filed on an even date herewith, and U.S. Provisional App. No. 62/643,366, filed on an even date herewith, each of which is hereby incorporated by reference in its entirety.

The intravascular imaging system 100 (or intraluminal imaging system) can be any type of imaging system suitable for use in the lumens or vasculature of a patient. In some embodiments, the intravascular imaging system 100 is an intravascular ultrasound (IVUS) imaging system. In other embodiments, the intravascular imaging system 100 may include systems configured for forward looking intravascular ultrasound (FL-IVUS) imaging, intravascular photoacoustic (IVPA) imaging, intracardiac echocardiography (ICE), transesophageal echocardiography (TEE), and/or other suitable imaging modalities.

It is understood that the system 100 and/or device 102 can be configured to obtain any suitable intravascular imaging data. In some embodiments, the device 102 can include an imaging component of any suitable imaging modality, such as optical imaging, optical coherence tomography (OCT), etc. In some embodiments, the device 102 can include any suitable imaging component, including a pressure sensor, a flow sensor, a temperature sensor, an optical fiber, a reflector, a mirror, a prism, an ablation element, a radio frequency (RF) electrode, a conductor, and/or combinations thereof. Generally, the device 102 can include a imaging element to obtain intravascular data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intravascular device 102, PIM 104, and monitor 108 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, the intravascular device 102 emits ultrasonic energy from a transducer array 124 included in scanner assembly 110 mounted near a distal end of the intravascular device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intravascular device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducers between 1 transducer and 1000 transducers, including values such as 2 transducers, 4 transducers, 36 transducers, 64 transducers, 128 transducers, 500 transducers, 812 transducers, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intravascular imaging system 100 described herein. For example, the processor can execute computer readable instructions stored on the non-transitory tangible computer readable medium.

The PIM 104 facilitates communication of signals between the processing system 106 and the scanner assembly 110 included in the intravascular device 102. This communication may include providing commands to integrated circuit controller chip(s) within the intravascular device 102, select particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intravascular device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or surrounded structures, both natural and man-made. Lumen 120 may be within a body of a patient. Lumen 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The processing system or controller 106 may include a processing circuit having one or more processors in communication with memory and/or other suitable tangible computer readable storage media. The processing system or controller 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intravascular device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intravascular device 102 my include the scanner assembly 110 near a distal end of the intravascular device 102 and a transmission line bundle 112 extending along the longitudinal body of the intravascular device 102. The cable or transmission line bundle 112 can include a plurality of conductors, including one, two, three, four, five, six, seven, or more conductors.

The transmission line bundle 112 terminates in a PIM connector 114 at a proximal end of the intravascular device 102. The PIM connector 114 electrically couples the transmission line bundle 112 to the PIM 104 and physically couples the intravascular device 102 to the PIM 104. In an embodiment, the intravascular device 102 further includes a guidewire exit port 116. Accordingly, in some instances the intravascular device 102 is a rapid-exchange catheter. The guidewire exit port 116 allows a guidewire 118 to be inserted towards the distal end in order to direct the intravascular device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intravascular imaging procedure. This workflow may include performing a pre-stent plan to determine the state of a lumen and potential for a stent, as well as checking on a stent that has been positioned in a lumen. The workflow may presented to a user as any of the displays or visualizations shown in FIGS. 2-9.

Figure 2:
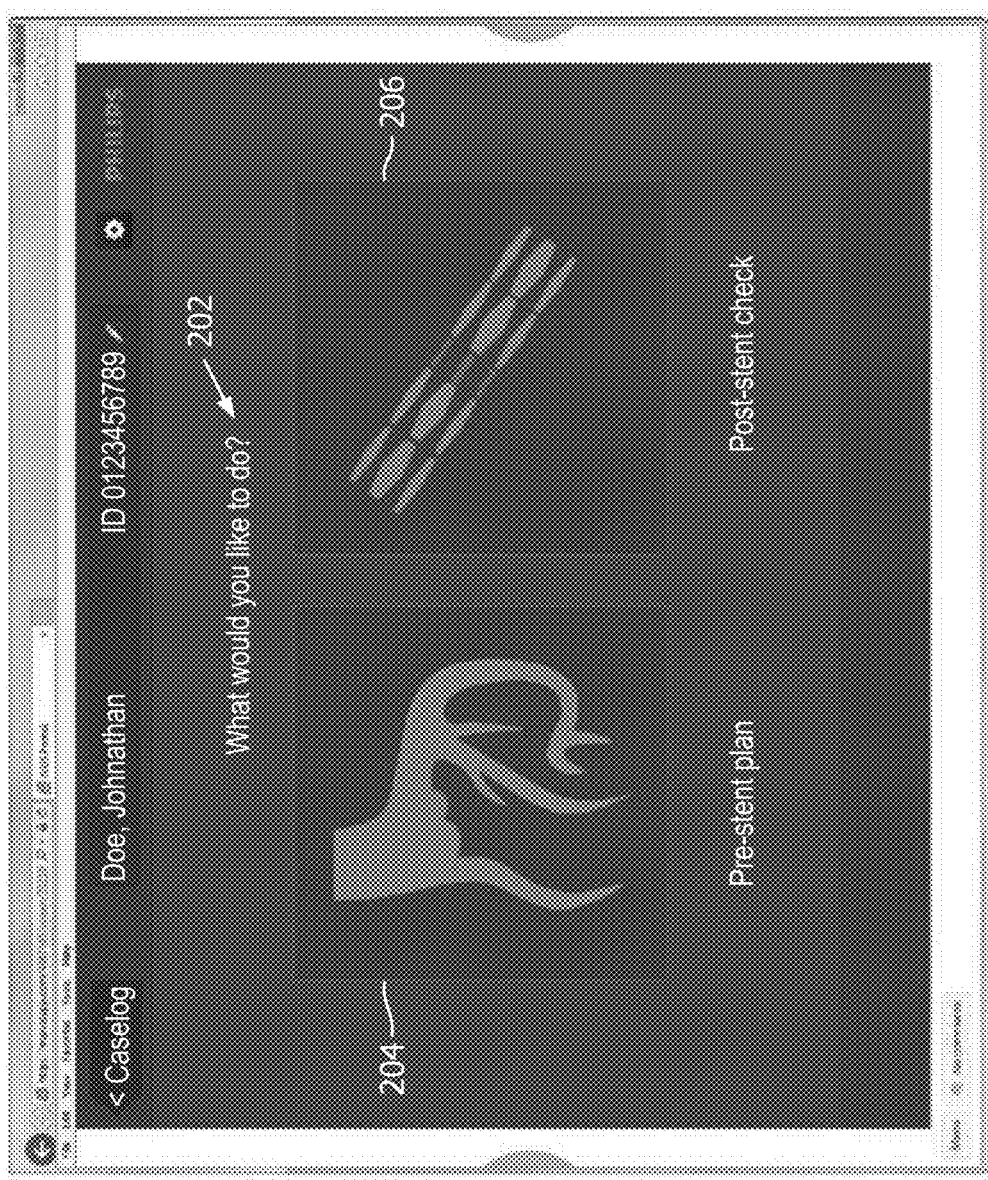
FIG. 2 is an exemplary illustration of a display showing a prompt according to aspects of the present disclosure.
Figure 2:

FIG. 2 shows an exemplary display 200 showing a prompt 202 according to aspects of the present disclosure. In some embodiments, the display 200 is displayed on the monitor 108 as shown in FIG. 1. In other embodiments, the display 200 is displayed on a screen of another device, such as PIM 104. The display 200 may be generated by a controller of the intravascular imaging system 100. In some embodiments, the display 200 is configured to display prompts and instructions as well as other data to an operator. The display 200 may be used to show a complete end-to-end workflow for an intravascular procedure. This workflow may include a number of prompts and instructions that may guide an operator through a procedure. This may simplify the steps of a procedure and help to avoid operator errors.

Figure 3:
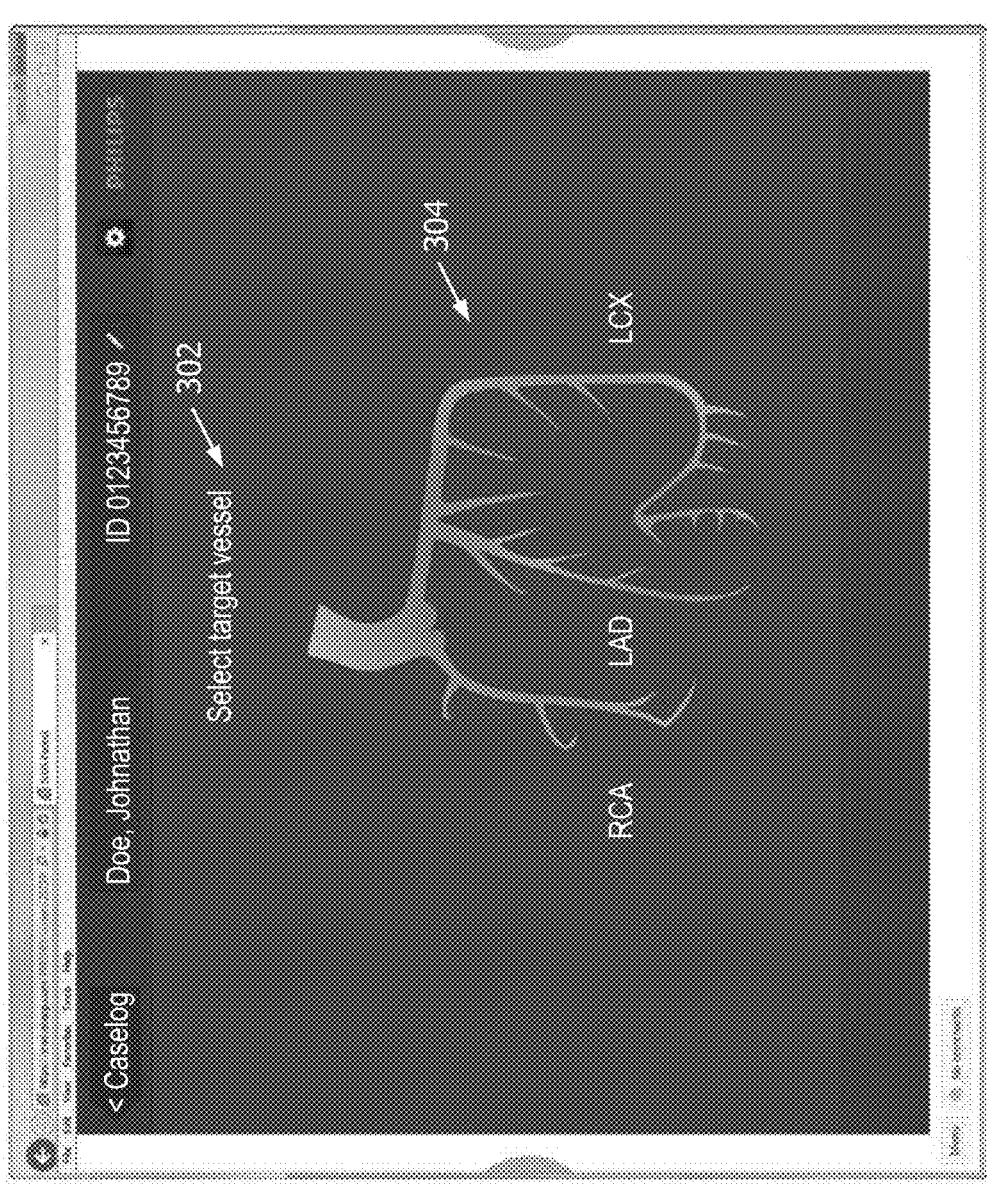
FIG. 3 is an exemplary illustration of a display showing another prompt according to aspects of the present disclosure.

The prompts and instructions may be displayed on the display 200 as selectable options such that an operator may interact with the display 200 to choose options. The selections of the operator may change the display 200 such that information corresponding with the selected options is shown. In the example of FIG. 1, a selectable prompt 202 is displayed on display 200. The prompt includes two selectable options: option 204 corresponds to a pre-stent plan and option 206 corresponds to a post-stent check. The operator may select one of the options 204, 206 which may move the workflow forward, such that other screens are displayed (such as prompt 302 as shown in FIG. 3). The options 204, 206 may include visual representations of the type of procedure. For example, option 204 may include a depiction of vasculature within the heart and option 206 may include a depiction of a stent. In some embodiments, the selection of an option 204, 206 may involve a change in the visual depiction of the option 204, 206. For example, if the pre-stent plan option 204 is selected, the option 204 may appear as shaded or grey in future displays of the display 200. This may help to indicate that this option 204 has previously been selected by an operator. Other types of feedback may be used to indicate selections of options. For example, the selectable options 204, 206 may display blinking areas, highlighted areas, altered colors, shading, altered transparencies, and other visual indicators.

Option 204 may provide a workflow for a pre-stent plan that may include performing an intravascular procedure (such as a pullback operation) and viewing results. Option 204 may be used to identify areas within a lumen 120 that may benefit from the placement of a stent. Option 206 may provide a workflow for a post-stent check that may include performing an intravascular procedure (such as a pullback operation) and viewing results of an area within a lumen 120 where a stent has previously been placed. This option 206 may be used to observe the placement and effectiveness of the stent.

FIG. 3 shows an exemplary display 200 showing a prompt 302 according to aspects of the present disclosure. The colors, shading, textures, and other graphical properties of the display 200 may be chosen to highlight specific features. In some embodiments, the prompt 302 may be displayed after either of the options 204, 206 are selected. In other embodiments, the prompt 302 is displayed only after the pre-stent plan option 204 is selected. The prompt 302 may prompt the operator to select a target vessel. In the example of FIG. 3, selecting the target vessel includes selecting a region on a visualization 304 including arteries in the heart. The selectable regions may include the right coronary artery (RCA), left anterior descending (LAD), and left circumflex artery (LCX). The selectable regions may also include various regions of the arteries, as well as other vessels and lumens within other parts of the anatomy of a patient. The appearance of the visualization 304 may be altered when one of the regions is selected by the operator. For example, the selected artery may be outlined, highlighted, or colored with a different color. In some embodiments, the selected artery is outlined in a contrasting color (e.g., blue, red, or another color), shaded, shown with a texture, or otherwise highlighted.

Figure 4:
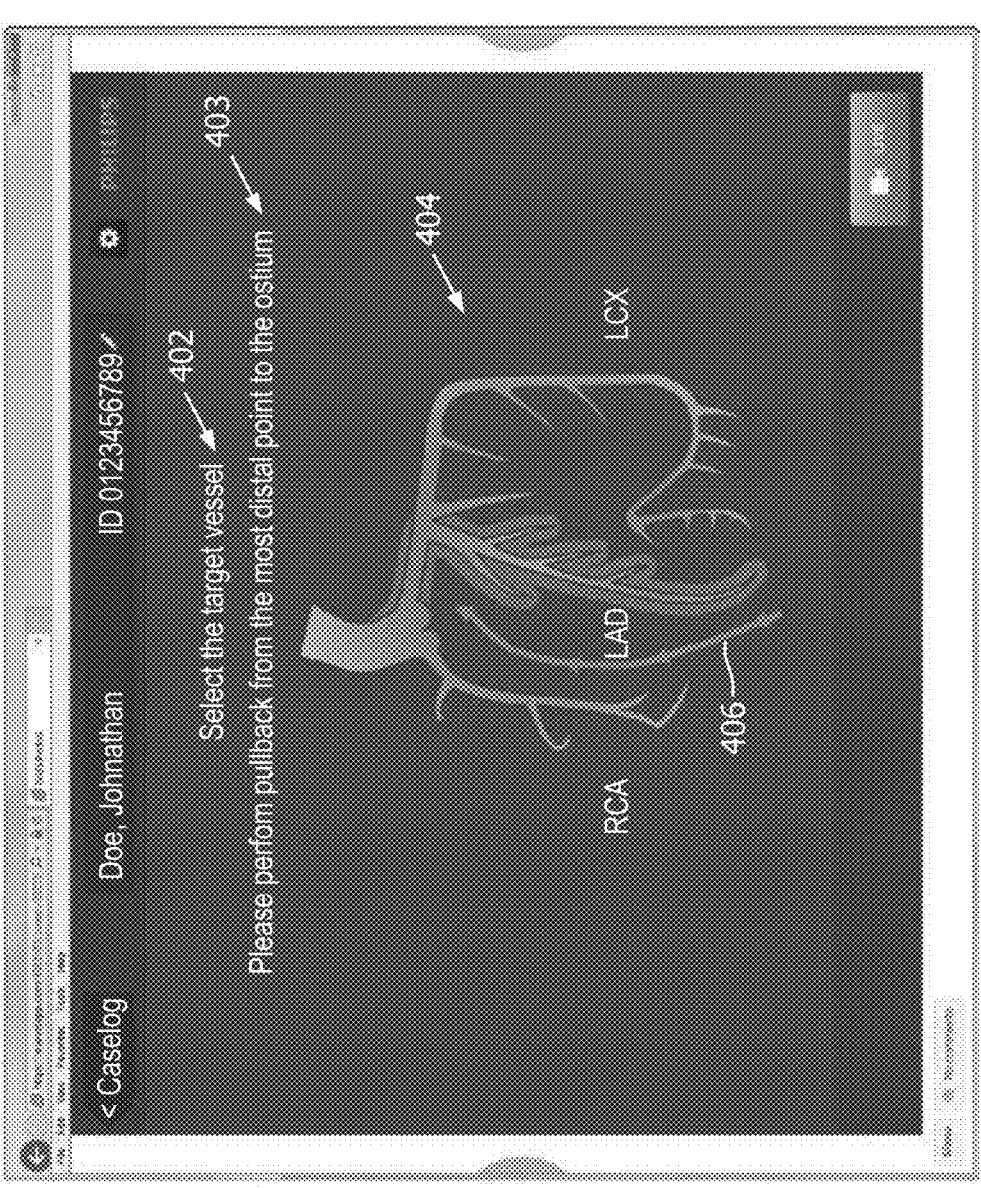
FIG. 4 is an exemplary illustration of a display showing another prompt and instructions according to aspects of the present disclosure.
Figure 4:

FIG. 4 shows an exemplary display 200 showing a prompt 402 according to aspects of the present disclosure. The prompt 402 may be displayed after the operator has made a selection on the prompt 302 shown in FIG. 3. In the example of FIG. 4, the LAD artery has been selected by an operator. The prompt 402 shows the outlined image of the LAD along with instructions 403 to perform a pullback procedure from the most distal point on the LAD to the ostium. These instructions 403 may refer to a pullback procedure or other movement of the device 102 within the selected vessel or lumen 120. The instructions 403 may instruct an operator to perform any type of movement of the device 102 within a selected target vessel. For example, the instructions 403 may instruct an operator to push the device 102 a given distance along the selected target vessel. A visualization 404 corresponding to the instructions 403 may also be displayed on the display 200. In the example of FIG. 4, the visualization 404 includes a line 406 with arrows showing the direction in which the pullback procedure should be performed. The visualization 404 may include visual effects such as changing colors or animation. For example, the arrows of the visualization 404 may move in the direction specified by the instructions 403. The instructions 403 and visualization 404 may vary depending on options that were previously selected. For example, if an operator selected the RCA as the target vessel, the visualization 404 of the RCA would be highlighted and a corresponding visualization would be displayed showing a procedure outlined by instructions 403.

In some embodiments, the instructions 403 of the display 200 may vary depending on which option 204, 206 was selected from the prompt 202 shown in FIG. 2. For example, if the post-stent check option 206 was selected, the instructions may read "please perform pullback from the distal point of the stent to the proximal point of the stent." Other instructions may also be included to guide the operator to perform an imaging procedure and acquire imaging data relevant to the selected target vessel and/or stent.

Figure 5:
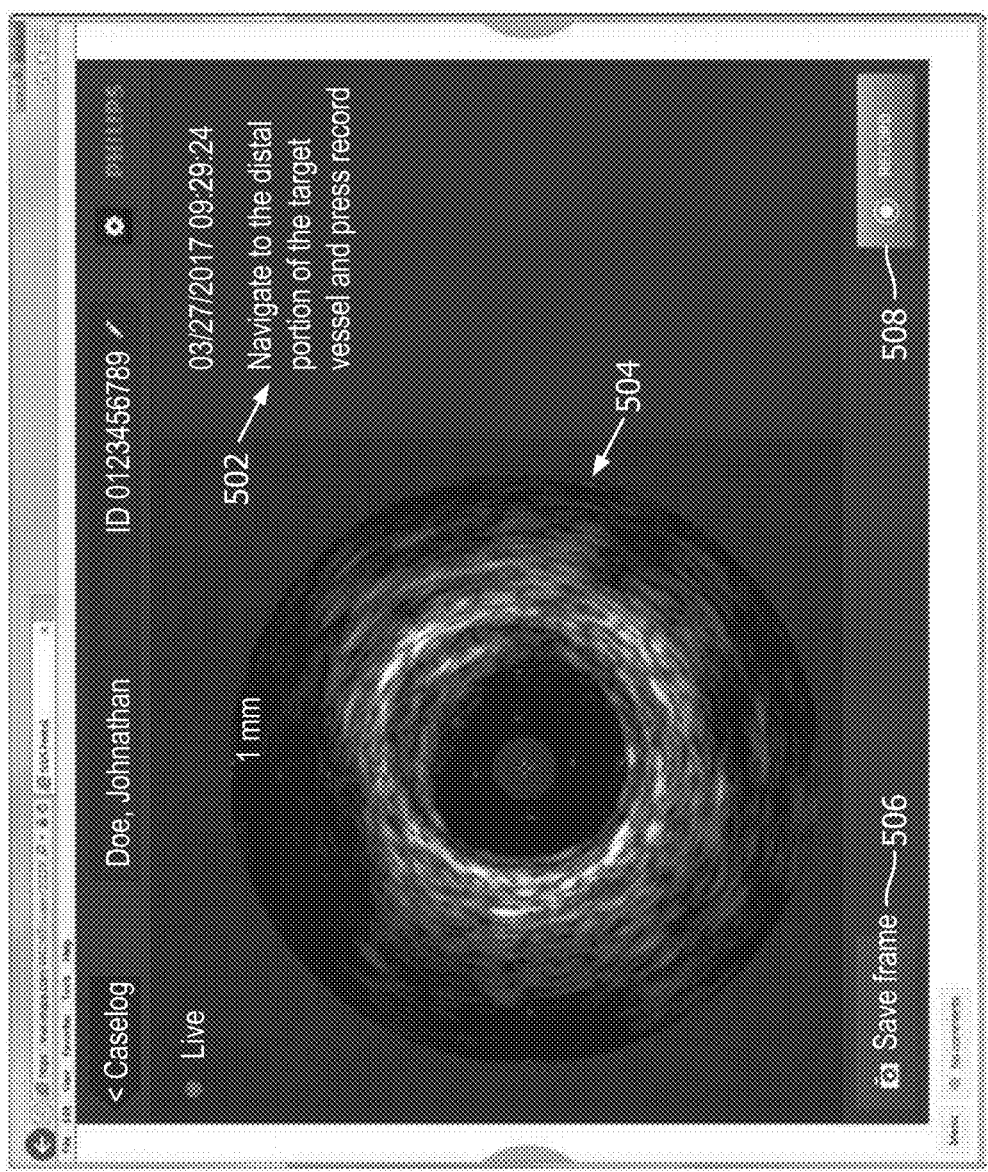
FIG. 5 is an exemplary illustration of a display showing imaging data and instructions according to aspects of the present disclosure.
Figure 5:

FIG. 5 shows an exemplary display 200 showing a prompt 502 according to aspects of the present disclosure. The prompt 502 may be displayed after the operator has made a selection on the prompt 402 shown in FIG. 4. In the example of FIG. 5, the LAD artery has been selected by an operator. The prompt 502 may be accompanied by a visualization 504. In some embodiments, the visualization 504 shows imaging data from the device 102 as the device 102 is moved through the selected target vessel. The imaging data may be used as a reference for the operator. In particular, imaging data shown in the visualization 504 may help the operator to know where to begin a procedure. In the example of FIG. 5, the imaging data may show when the device 102 is positioned at a distal end of the LAD artery so that a pullback operation may be performed. The imaging data may also show other reference data such as areas of interest along a lumen 120, branches of the lumen 120, problem areas within the lumen 120, or other features. In some embodiments, when the device 102 is placed at the location specified by the instructions (for example, at a distal portion of an artery), the operator may select the record button 508 to begin a recording of the procedure. The display may also include an option 506 to save specific frames of imaging data before or during a procedure.

Figure 6:
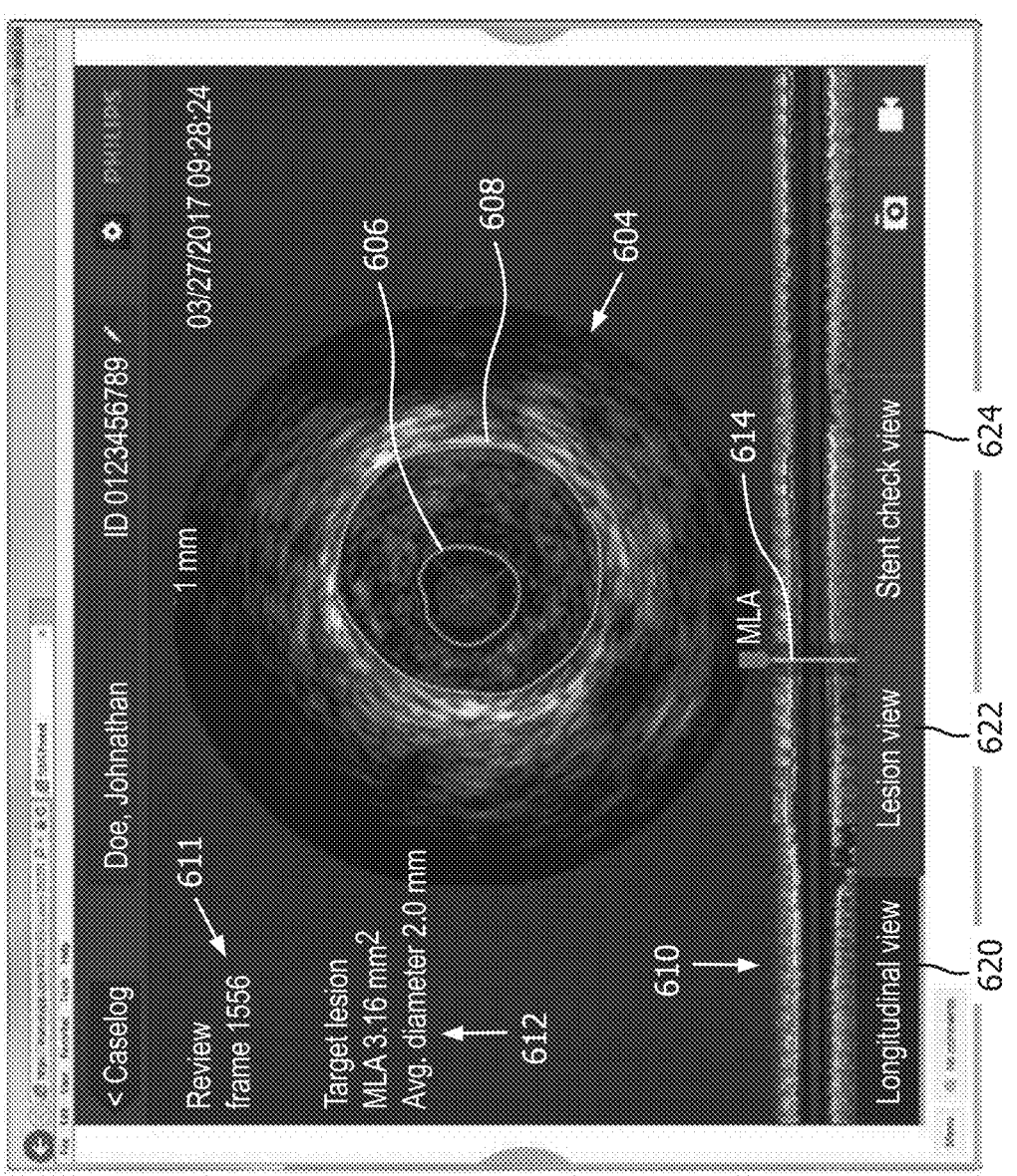
FIG. 6 is an exemplary illustration of a display showing imaging data according to aspects of the present disclosure.
Figure 6:

FIG. 6 shows an exemplary visualization 310 according to aspects of the present disclosure. The visualization 310 may be displayed on a monitor 108. The visualization 310 may present imaging data acquired by the device 102 during an intravascular procedure. In some embodiments, the intravascular procedure is outlined in the instructions shown in FIGS. 3-5. In some embodiments, the visualization 310 includes imaging data corresponding to a lumen 120, such as the selected target vessel. The visualization 310 may include a first view 604 and a second view 610 of the lumen 120. In some embodiments, the first and second views 604, 610 may be oriented 90 degrees apart. In the example of FIG. 6, the first view 604 shows imaging data corresponding to a view straight down the lumen 120 (otherwise discussed as a "longitudinal view") and the second view 610 shows imaging data corresponding to a transverse view of the lumen 120. In other embodiments, other views may also be shown. For example, in FIGS. 7A-7C, three different views are shown, including a third view 704 showing a three dimensional sectional view of the lumen 120. The views 604, 610 may include corresponding imaging data.

In some embodiments, the visualization 310 may include a selected frame of imaging data received by the device 102. For example, text box 611 states that the visualization 310 corresponds to frame 1556 in the example of FIG. 6. The operator may be able to select any frame from the imaging data received by the device 102. This may allow the operator to focus on specific areas of interest in the lumen 120.

In some embodiments, measurements are performed automatically on the imaging data with a controller of the intravascular imaging system 100 as the imaging data is acquired by the device 102. In the example of FIG. 6, measurements corresponding to a vessel boundary 608 and a minimum lumen area (MLA) 606 are displayed on the first view 604. The measurements may also include a vessel diameter, a center of the vessel, a vessel boundary 608 thickness, and other measurements performed automatically by the controller. These measurements may also be shown on other views. For example, a marker 614 is placed at the MLA in the second view 610 that corresponds with the MLA 606 in the first view 604. This may help an operator to visualize the diameter of vessel boundaries along the lumen 120. The measurements may be displayed in numerical format at box 612 on the visualization 310.

Figure 8:
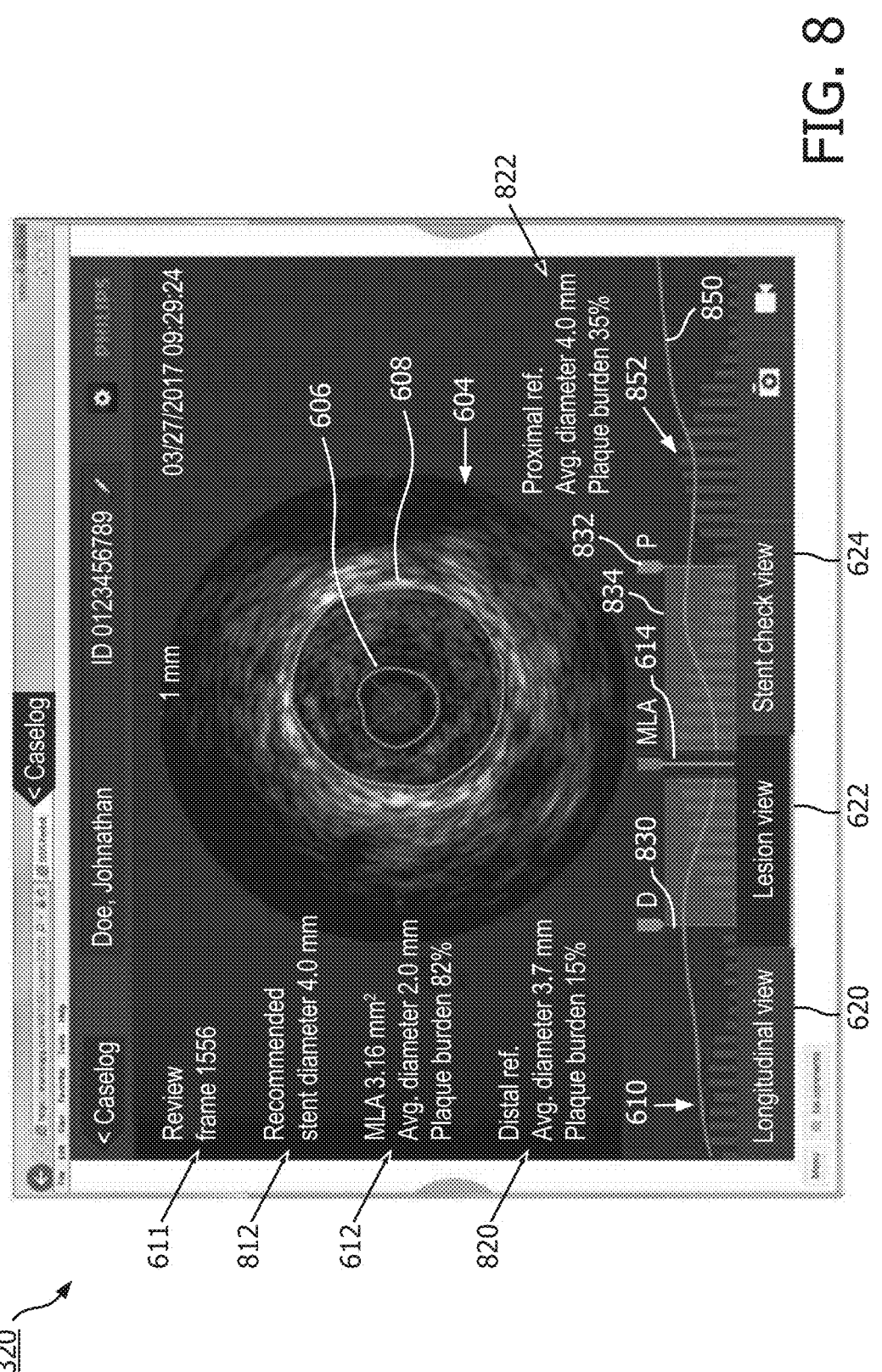
FIG. 8 is an exemplary illustration of a display showing imaging data according to aspects of the present disclosure.
Figure 9:
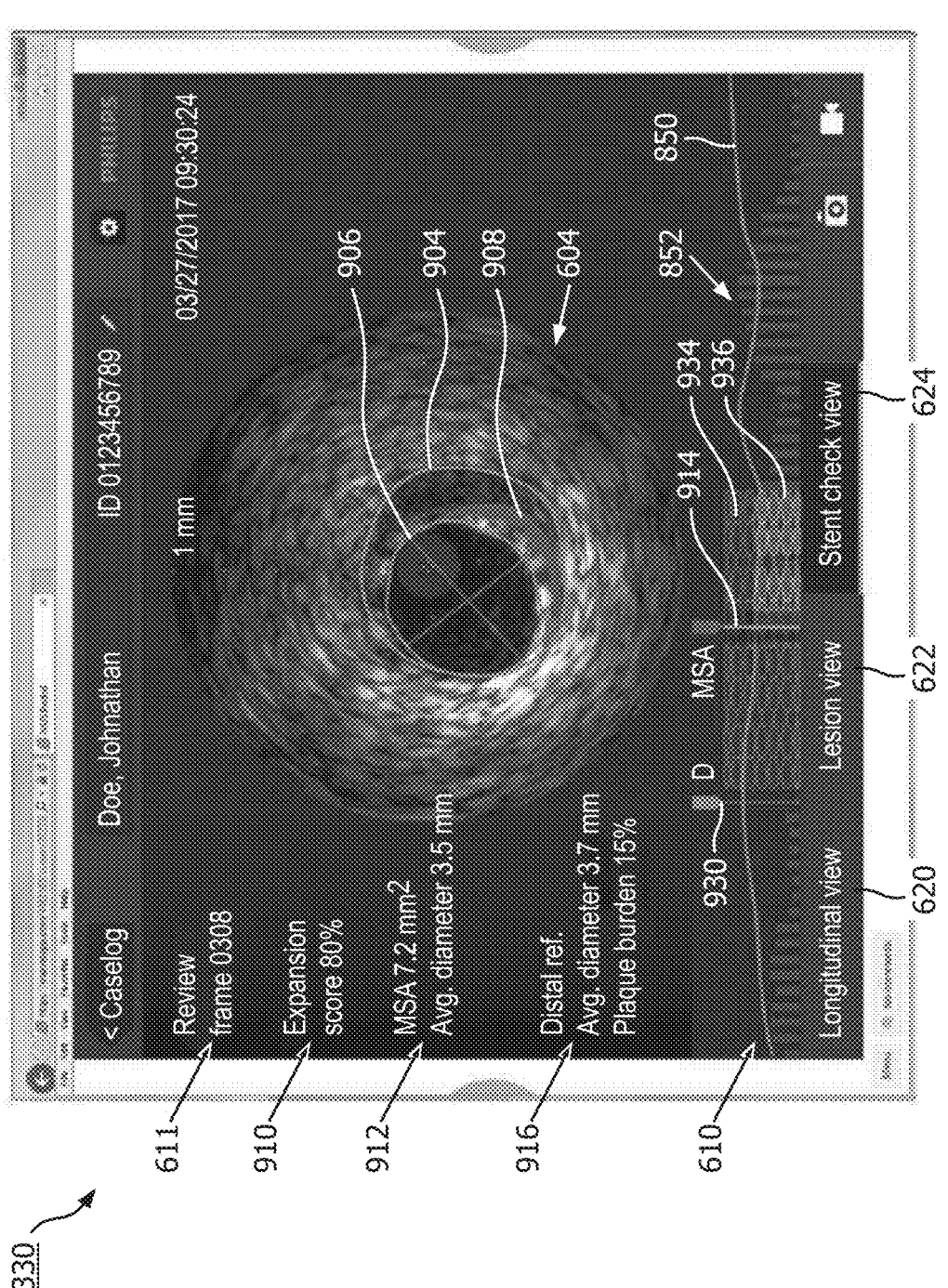
FIG. 9 is an exemplary illustration of a display showing imaging data according to aspects of the present disclosure.

Specific portions and views of the visualization 300 may be viewed by an operator by selecting the options 620, 622, and 624. In some embodiments, option 620 corresponds with the visualization 310 shown in FIG. 6, option 622 corresponds with the visualization 320 shown in FIG. 8, and option 624 corresponds with the visualization 330 shown in FIG. 9. An operator may select option 620 to view a longitudinal view of the lumen 120, option 622 to view a view of a lesion in the lumen 120, and option 624 to view a stent and surrounding portion of the lumen 120. In some embodiments, the primary view or first view 604 of each option 620, 622, 624 is accompanied by a transverse view 610 of the lumen 120 as shown in FIGS. 6, 8, and 9.

Figure 7A:
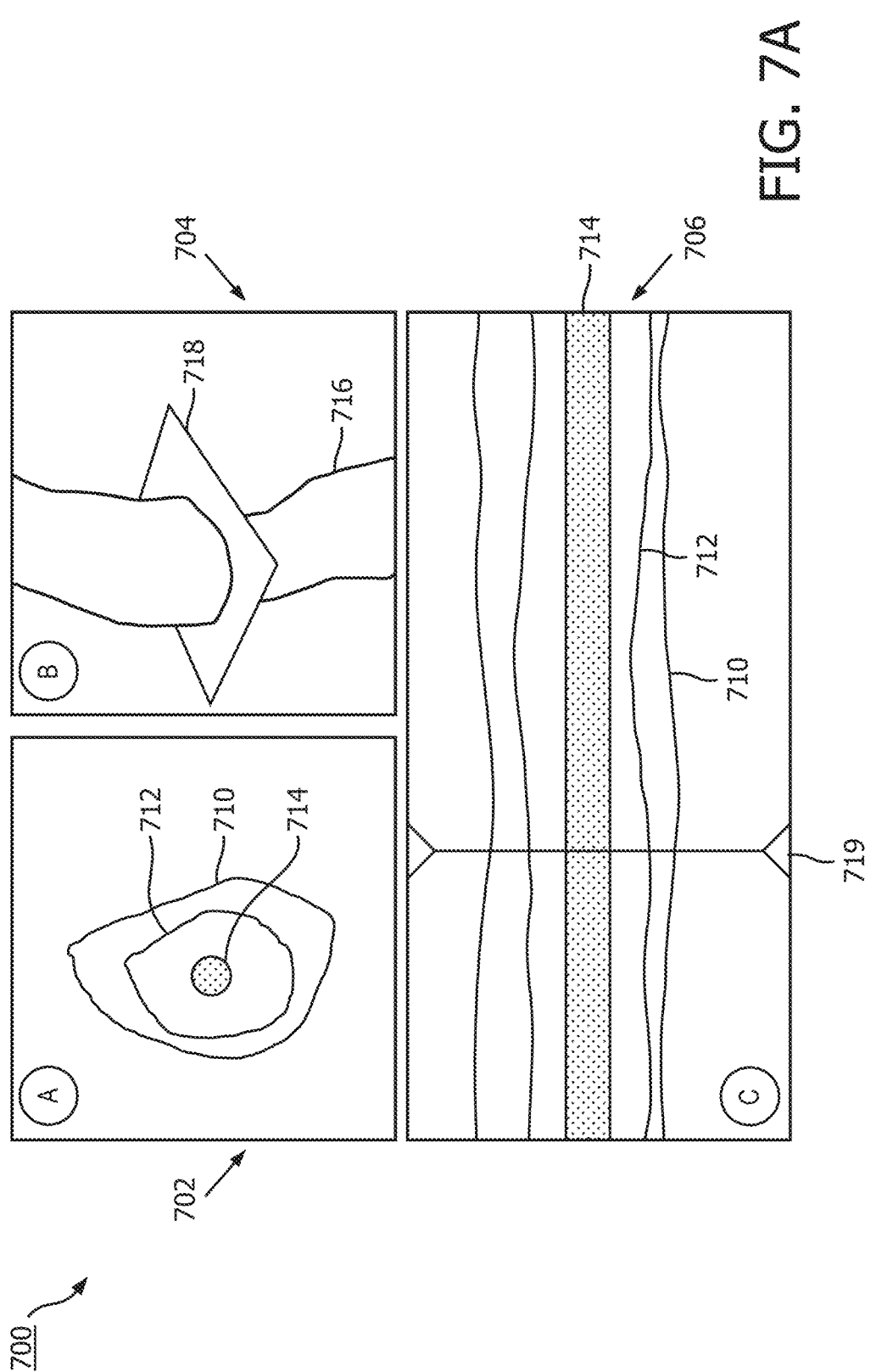
FIG. 7A is an exemplary illustration of a display showing various views of imaging data according to aspects of the present disclosure.
Figure 7B:
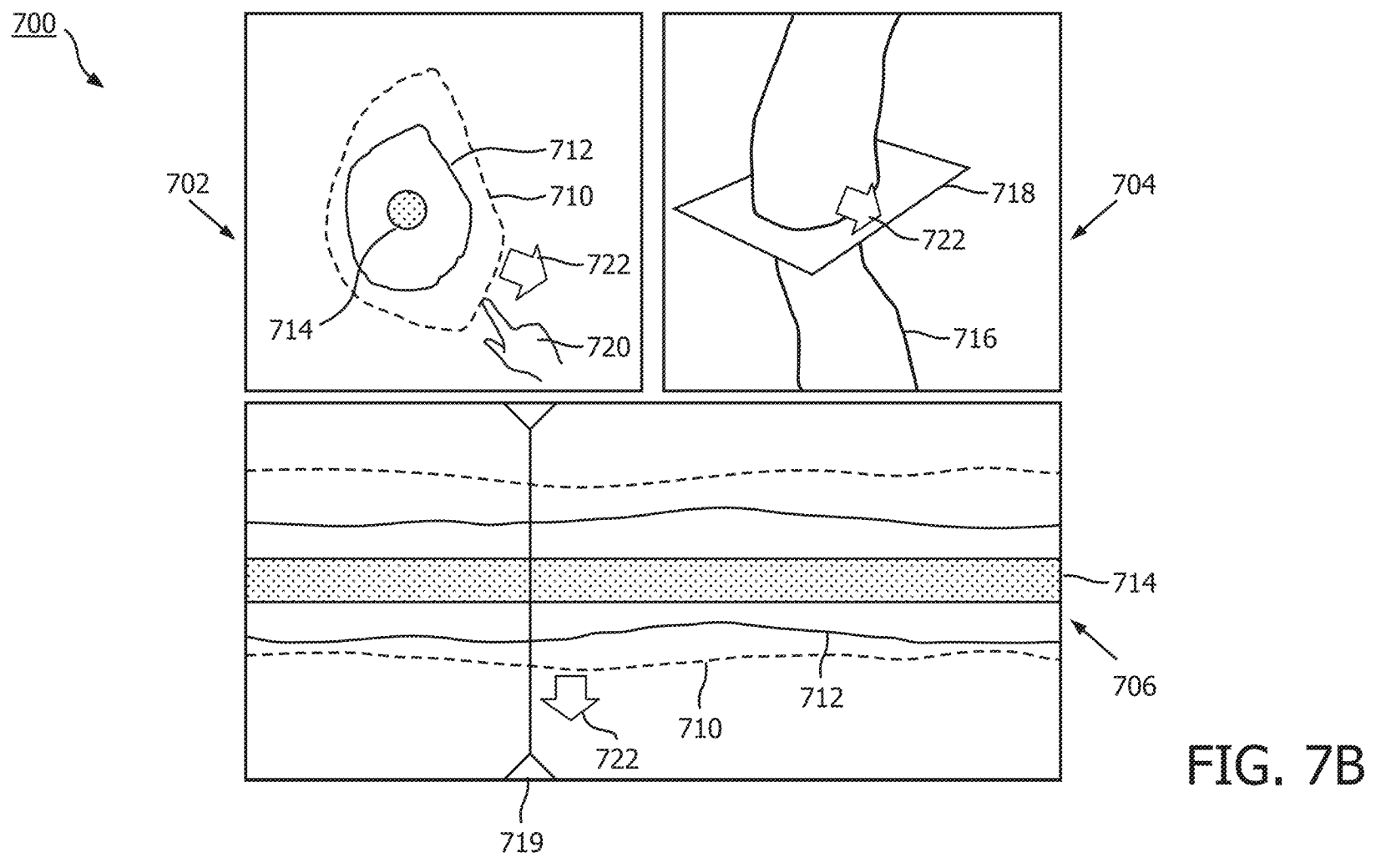
Figure 7C:
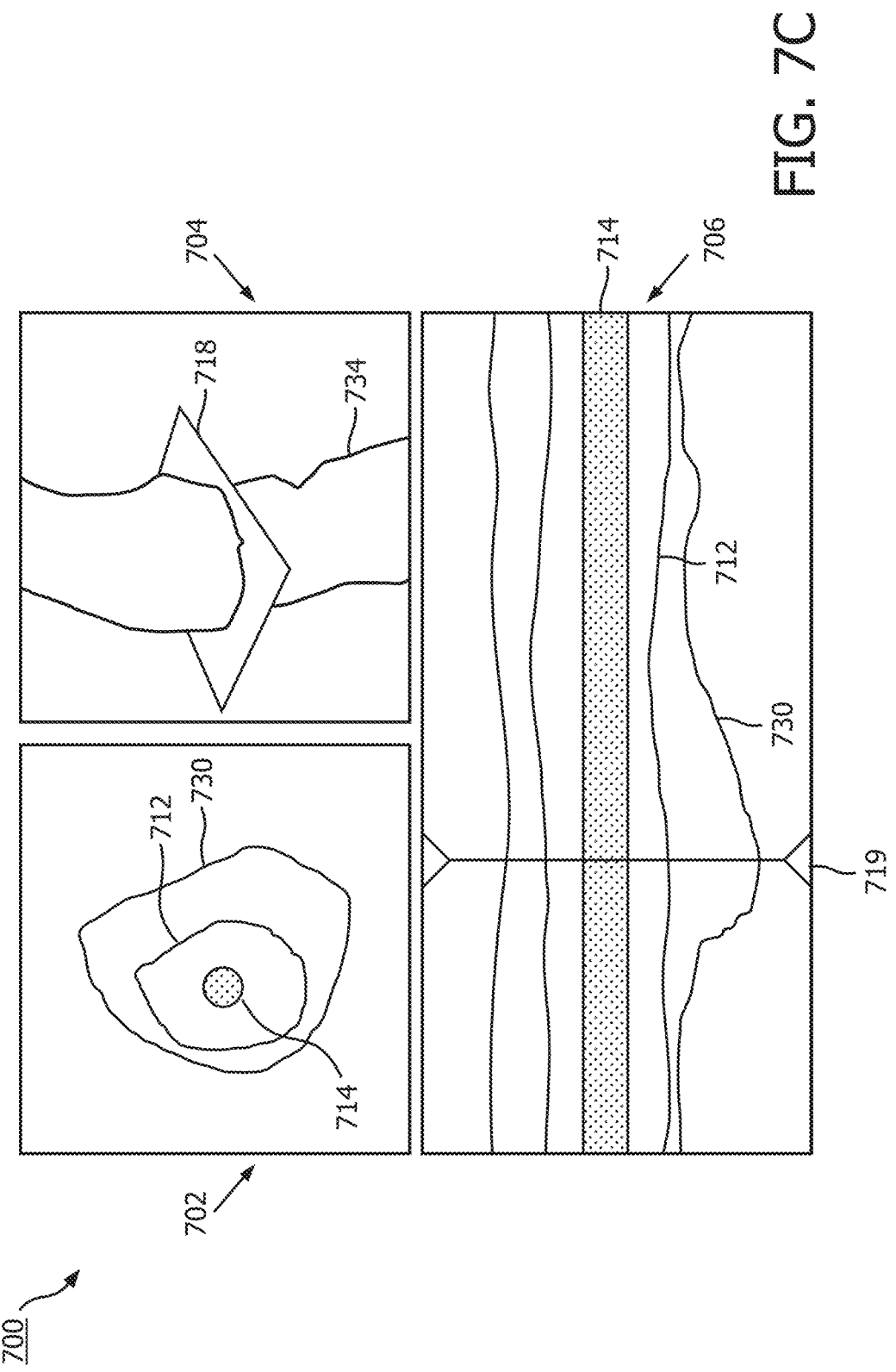
FIG. 7C is an exemplary illustration of another display showing various views of imaging data according to aspects of the present disclosure.

FIGS. 7A-7C show an exemplary display 700 with various views showing imaging data according to aspects of the present disclosure. The display 700 may be displayed on the monitor 108. FIG. 7A shows a display 700 with three different views 702, 704, 706 of imaging data. In some embodiments, view 702 is a longitudinal view of a lumen 120, view 704 is a three dimensional cross section of the lumen 120, and view 706 is a transverse view of the lumen 120. The views 702 may include visualization of boundaries 710, 712, 714, 716 of aspects of the lumen. For example, boundary 710 may represent a vessel boundary, boundary 712 may represent a MLA of a portion of the lumen 120, boundary 714 may represent a central area of the lumen 120 and boundary 716 may represent a three dimensional vessel boundary. Furthermore, planes 718 and 719 may represent planes along which view 702 is viewed. The boundaries 710, 712, 714, 716 in one view may correspond with the boundaries 710, 712, 714, 716 in the other views 702, 704, 706 of the display 700. The presentation of different views may help an operator to visualize the size and shape of portions of the lumen 120.

FIG. 7B shows an exemplary display 700 with a function to allow the operator to edit one or more of the visualization of the boundaries 710, 712, 714, 716. In the example of FIG. 7B, the operator may use a tool 720 to select a boundary to move (in this case, boundary 710). The selected boundary may appear as a dotted line. The boundary may be moved in any direction. In the example of FIG. 7B, an arrow 722 shows the direction that the boundary is moved (i.e., in an outward direction). A corresponding movement of the boundary is also shown in views 702, 706, along with arrows 722 to show the direction of movement. The operator may move the boundaries 710, 712, 714, 716 to correct errors in imaging data or to visualize potential outcomes of procedures (such as inserting a stent in a lumen 120).

FIG. 7C shows an exemplary display 700 after the boundary 710 has been moved to a new location at boundary 730. As discussed above, the views 702, 704, 706 show corresponding boundaries 730, 734 that an operator can view together to better understand the shape of a portion of a lumen 120.

FIG. 8 shows an exemplary visualization 320 showing a lesion view according to aspects of the present disclosure. In some embodiments, visualization 320 corresponds to the pre-stent plan option 204 as shown in FIG. 2. In some embodiments, the visualization 320 may be used to recommend the placement and size of a stent to address a lesion. These recommendations may be made automatically by the system 100 based on the imaging data received by the device 102. In particular, the visualization 320 may be used to visualize a portion of a lumen 120 with a potential "landing zone" 834 for a stent. In some embodiments, the landing zone 834 is an area of interest within the lumen 120 that includes an MLA of a portion of the lumen 120, as marked by marker 614. The landing zone 834 may be shown in profile in view 610 to show the potential placement of the stent within the landing zone 834. A distal end marker 830 and a proximal end marker 832 of the landing zone 834 may define the distal and proximal extent of a potential stent. The distal end marker 830 and proximal end marker 832 may be accompanied with numerical data 820, 822 illustrating the average diameter and plaque burden of the lumen 120 at these locations. In some embodiments, the visualization may also a depiction of the plaque burden 852 along the lumen 120. In some embodiments, the depiction of the plaque burden 852 is automatically measured based on imaging data from the device 102. The visualization 320 may also include a depiction of lumen area 850. As illustrated in FIG. 8, the marker 614 for the MLA may be placed where the plaque burden is the greatest and the area of the lumen is the smallest.

In some embodiments, the visualization 320 includes a recommended stent diameter as shown in text box 812. This diameter may be based on the diameter of the lumen 102 as measured by the system 100.

FIG. 9 shows an exemplary visualization 330 showing a stent check view according to aspects of the present disclosure. In some embodiments, the visualization 330 is shown after the operator has selected the stent check option 204 and has been guided through the subsequent workflow steps. The visualization 330 may display imaging data gathered from the device 102 during motion within a lumen 120 (such as a pullback procedure) where a stent has been placed, as well as imaging data of surrounding areas of the lumen.

Measurements and/or metrics corresponding to the imaging data may be performed automatically by the intravascular imaging system and displayed by the visualization 330. For example, the intravascular imaging system 100 may be used to perform length measurements such as minimum, maximum, average, and mean lengths of features in the imaging data. The effective diameter of features may also be measured. Area measurements of features such as lumens, vessels, plaque, and thrombus may be performed by the intravascular imaging system 100. The measurements may include plaque burden, percent stenosis, percent difference, diameter stenosis, percent diameter stenosis, luminal gain, and luminal gain percentage. Furthermore, features of a stent may also be measured by the intravascular imaging system 100, including overall stent area, minimum stent area, average stent area, stent apposition, expansion, malapposition, and a stent score. The visualization 330 can include numerical values of one or more of these measurements or other graphical representations (e.g., shading, coloring, etc.), including graphical representations overlaid on or displayed separately/spaced from tomographic, longitudinal, and/or angiographic images of a vessel.

In some embodiments, the shape and size of a lumen boundary 904 may be measured and displayed, as well a boundary of the stent 906. As in FIGS. 6 and 8, the boundaries may be visualized in a first view 604 as well as a second view 610. The visualization 330 may also include measurements of the length of the stent. For example, the visualization 330 may include a distal reference marker 930 and may include a depiction 934 of the stent. The average diameter and plaque burden at the distal reference marker may be shown in text box 916. The minimum stent area (MSA) may also be automatically measured and displayed in the text box 912 as well as with MSA marker 914.

In some embodiments, the visualization 330 may be used to determine the effectiveness of a stent. For example, the visualization 330 may include measurements and depictions of any malapposition of the stent. The malapposition areas 908, 936 may be shown in both the first view 604 and the second view 610 so that an operator can better visualize the malapposition. The malapposition areas 908, 936 may have a different color than other imaging data (such as red) to highlight this feature. In some embodiments, the malapposition areas 908, 936 are measured automatically using the imaging data collected by the device 102 during a pullback procedure of the stent. The visualization 330 may also include an expansion score 910. In the example of FIG. 9, the expansion score is 80%. This may signify that the stent is mostly expanded to contact the lumen 120, but a malapposition is present. In some embodiments, the expansion score may vary from 0% (where a stent is not yet extended within the stent) to 100% (where a stent is completely expanded and no malappositions are present). The expansion score 910 may be determined automatically with the controller of the system 100 by comparing measurements of the border of the stent 906 to the borders of the lumen. In some embodiments, the expansion score 910 is also based on the plaque burden and lumen area within the vessel.

FIG. 10 is a flow diagram of a method 1000 of proving a guided workflow for an intravascular imaging procedure to a user. In some embodiments, the steps of the method 1000 may be carried out by the intravascular imaging system 100 and associated components as shown in FIG. 1. It is understood that the steps of method 1000 may be performed in a different order than shown in FIG. 10, additional steps can be provided before, during, and after the steps, and/or some of the steps described can be replaced or eliminated in other embodiments.

At step 1002, the method 1000 may include providing a guided workflow to a user. The guided workflow may be provided as a series of prompts, instructions, and visualizations that are displayed on a display device, such as monitor 108 as shown in FIG. 1. The guided workflow may help a user to easily and accurately perform each step of an intravascular imaging procedure. The guided workflow may present different options based on the selections of the user and may include checks of previous steps to ensure that all steps of the procedure have been performed.

At step 1004, the method may include providing a selectable option for a pre-stent plan or a post-stent check. The selectable option may be provided on a display such as display 200 as shown in FIG. 2. The selectable option for the pre-stent plan may include performing an intravascular imaging procedure to visualize a vessel or lumen before inserting a stent. The selectable option for the post-stent check may include performing an intravascular imaging procedure to check a stent that has been inserted in a vessel or lumen. Each selectable option may include a number of subsequent steps, as discussed below.

At step 1006, the method 1000 may include providing an option to select a target vessel. This option may be presented visually, such as presenting various vessels on a diagram. In some embodiments, the target vessels are arteries within the heart, such as the RCA, LAD, and LCX. In other embodiments, the target vessels are other lumens within the body. This step 1006 may involve providing feedback to a user, such as indicating which vessel has been selected. The feedback may include highlighting, coloring, shading or otherwise indicating the vessel that has been selected.

At step 1008, the method 1000 may include providing a prompt to perform an operation within the selected target vessel. In some embodiments, this operation includes moving an intravascular device within the vessel. For example, the operation may be a pullback operation. In other embodiments, the operation may be an operation to push an intravascular device through a portion of a lumen. The prompt may be presented in text format and may include a visualization of the operation.

At step 1010, the method 1000 may include providing a prompt to navigate an intravascular device to a starting point in the selected target vessel and activate sensors in the intravascular device. This prompt may be presented with text as well as images showing where the user should place the intravascular device. In some embodiments, the prompt of step 1010 depends on the option selected at step 1004. For example, if the user selected the pre-stent plan option at step 1004, the prompt at step 1010 may prompt the user to navigate the intravascular device from a most distal point of the target vessel to the ostium. If the user selected the post-stent check option at step 1004, the prompt at step 1010 may prompt the user to navigate the intravascular device from a distal end of the stent to a proximal end of the stent.

At step 1012, the method 1000 may include receiving imaging data from the intravascular device. This imaging data may help a user to accurately navigate the intravascular device according to the prompt of step 1010. For example, if the prompt of step 1010 directs the user to navigate the intravascular device from a distal end of the stent to a proximal end of the stent, the imaging data may show imaging data from the intravascular device as it is moved to the distal end of the stent. In some embodiments, the imaging data may include IVUS data showing the layers of tissue on the interior of the vessel. In other embodiments, the imaging data includes data from another modality such as OCT. Thus, the imaging data may help the user to accurately perform the operation outlined in the prompt.

At step 1014, the method 1000 may include displaying the imaging data as the intravascular device is moved during the operation. This imaging data may help a user to accurately perform the operation.

At step 1016, the method 1000 may include identifying an area of interest using the imaging data. In some embodiment, the area of interest is identified based on imaging data such as border measurements, lumen area, plaque burden within the lumen, etc. The area of interest may include an MLA or MSA as shown in FIGS. 6, 8, and 9. In some embodiments, the area of interest includes a landing zone for stent placement or a stent that has been positioned in a lumen. The area of interest may be colored, highlighted, shaded, or otherwise indicated as an area of interest on a display of the imaging data. In some embodiments, the distal and proximal ends of the area of interest are shown as well as measurements of the size and position of the area of interest.

At step 1018, the method 1000 may include displaying vessel measurements based on the imaging data corresponding with the area of interest. In some embodiments, vessel measurements such as vessel boundaries, stent boundaries, MLA, MSA, lumen area, plaque burden, and other measurements are displayed on the display. These measurements may be shown graphically (for example, by colored lines or regions) as well as textually (for example, in text boxes). The vessel measurements may also include recommendations (such as the recommended size and position of stents) and scores (such as stent expansion scores). The vessel measurements may allow a user to quickly identify problem areas within a lumen as well as possible solutions.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus, comprising:

a processor configured for communication with an intravascular imaging device, wherein the processor is configured to:

receive a plurality of intravascular images obtained by the intravascular imaging device while the intravascular imaging device is moved through a blood vessel of a patient, wherein the blood vessel comprises a target area for treatment;

generate, based on the plurality of intravascular images, a screen display comprising:

a longitudinal representation of the blood vessel;

a first marker overlaid on the longitudinal representation at a first location comprising a distal reference;

a second marker overlaid on the longitudinal representation at a second location comprising a proximal reference;

a first numerical value of plaque burden distinct from the first marker and representative of the first location comprising the distal reference; and a second numerical value of plaque burden distinct from the second marker and representative of the second location comprising the proximal reference, wherein the first location and the second location are spaced from a third location comprising a minimum lumen measurement such that the distal reference is distal of the minimum lumen measurement and the proximal reference is proximal of the minimum lumen measurement, and output, to a display device in communication with the processor, the screen display for a user to plan the treatment of the target area, wherein the first marker, the second marker, the first numerical value of plaque burden, and the second numerical value of plaque burden are displayed simultaneously.

2. The apparatus of claim 1, wherein the screen display further comprises a third numerical value of plaque burden representative of the third location.

3. The apparatus of claim 1, wherein the first and second numerical values of plaque burden comprise percentages.

4. The apparatus of claim 1, wherein the first and second numerical values of plaque burden are distinct from values of percent stenosis.

5. The apparatus of claim 1, wherein the screen display further comprises a region overlaid on a first portion of the longitudinal view and representative of the target area, wherein region is defined between the first marker and the second marker, wherein the region is visually distinguished from a second portion of the longitudinal view.

6. The apparatus of claim 1, wherein the longitudinal representation comprises a plurality of bars of varying size.

7. The apparatus of claim 6, wherein the plurality of bars of varying size is representative of a plurality of numerical values of plaque burden along a length of the blood vessel.

8. The apparatus of claim 1, wherein the longitudinal representation comprises a two-dimensional curve representative of a plurality of numerical values of lumen area.

9. The apparatus of claim 1, further comprising the intravascular imaging device.

10. The apparatus of claim 1, further comprising the display device.

11. The apparatus of claim 1, wherein the treatment comprises a stent configured to extend across the target area and extend between the proximal reference and the distal reference.

12. The apparatus of claim 1, wherein a third numerical value of plaque burden at the third location is relatively larger than the first numerical value of plaque burden and the second numerical value of plaque burden.

13. The apparatus of claim 1, wherein the third location comprises a largest plaque burden.

* * * * *